United States Patent
Wenz et al.

(10) Patent No.: US 6,495,156 B2
(45) Date of Patent: Dec. 17, 2002

(54) BIOCEMENTS HAVING IMPROVED COMPRESSIVE STRENGTH

(75) Inventors: Robert Wenz, Wöllstadt (DE); Ferdinand Driessens, ohe en Laak (NL)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 09/853,042

(22) Filed: May 11, 2001

(65) Prior Publication Data

US 2002/0017220 A1 Feb. 14, 2002

(51) Int. Cl.⁷ .................................................. A61F 2/28
(52) U.S. Cl. ....................................... 424/426; 523/115
(58) Field of Search ...................... 424/426; 623/16.11; 523/115

(56) References Cited

U.S. PATENT DOCUMENTS 5,782,971 A * 7/1998 Constantz et al.

FOREIGN PATENT DOCUMENTS

WO   WO 99/49906   10/1999

* cited by examiner

*Primary Examiner*—Carlos Azpuru
(74) *Attorney, Agent, or Firm*—Millen, White, Zelano & Branigan, P.C.

(57) ABSTRACT

The invention describes biodegradable calcium phosphate cements, in particular mixtures of calcium phosphate-containing powders of different stoichiometric composition, the precipitated hydroxylapatite present being a cation-deficient hydroxylapatite of the formula 1, with the result that the mixtures have improved properties with regard to compressive strength.

23 Claims, No Drawings

BIOCEMENTS HAVING IMPROVED COMPRESSIVE STRENGTH

The prior German Patent Application P 198 13 614.5 relates to biodegradable calcium phosphate cements, in particular mixtures of calcium phosphate-containing powders of different stoichiometric composition having improved properties. These mixtures all comprise tricalcium phosphate (TCP) and one or more other phosphate-containing inorganic compounds of different composition, the TCP content being present in a well-defined particle size range. Essential for the invention was the fact that a specific fraction of fine particles (about 1–40 μm) and very fine particles (0.1–1 μm) must be present in addition to a specific fraction of coarse particles (40–300 μm).

A teaching of the present invention is based on the object of further improving biodegradable calcium phosphate cements of the type described. Here, the following considerations are particularly important: Up to the end of 1997, only prototypes of biocement D (for composition, cf. DE 19813614.5) were known. Characteristic of these prototypes were their adequate properties with respect to miscibility, cohesion time, dough time and initial and final hardening time according to ASTM C266, but the compressive strength never reached values greater than 50 MPa. It was thus only in the region of trabecular human bone (Driessens et al., Bioceramics 10 (1997) 279–282). Commercial TCP was used as the crystallization nucleus (cf. DE 19813614.5).

An object of the present invention is to achieve biocements having compressive strengths>50 MPa, which are even in the region of the cortical bone with respect to strength, without these biocements exhibiting adverse changes with regard to processing times and cohesion.

Upon further study of the specification and appended claims, further objects and advantages of this invention will become apparent to those skilled in the art.

This and other objects are achieved, according to the invention, by using a specially prepared, precipitated hydroxylapatite (PHA), this serving as a crystallization nucleus or nucleating agent for the formation of the carbonized apatite, formed during the hardening reaction, from biocement D. Surprisingly, it is thus possible to achieve compressive strengths of 70–80 MPa after the hardening (cf. Tab. 1 and FIG. 1).

An aspect of the present invention thus relates to a mixture of powders which are suitable for the preparation of absorbable calcium phosphate cements, comprising tricalcium phosphate (TCP) in which about 30–70% of the TCP particles have a particle size of about 0.1–7 μm and about 10–60% have a particle size of about 40–100 μm, precipitated hydroxylapatite (PHA) and at least one further other phosphate-containing inorganic compound, the PHA being a cation-deficient hydroxylapatite having the composition $$Ca_{8.75}V(Ca)_{1.25}[(HPO_4)_{5.5-x}(CO_3)_{0.5}](OH)_xV(OH)_{2-x}$$

with values for x between 0 and 2.

It was found that the precipitate formed during the setting and hardening phase from biocement D is a carbonized cation-deficient hydroxylapatite of the above-mentioned empirical formula. V(Ca) and V(OH) are Ca and OH voids in the crystal lattice. The values for x depend in turn on the structurally related water content of the apatite. It was furthermore found that the structure and composition of the PHA used to date as a nucleus for the preparation of the biocement D prototype, the so-called TCP, differs considerably from those of the cation-deficient hydroxylapatite described above. The TCP used in the prior art (cf. DE 198 13614) comprises, as the main phase, apatite which however comprises very little carbonate ($CO_2$ content<0.2%) and, as secondary phases, monetite. This led to the conclusion that it is necessary to prepare a more highly carbonized, precipitated cation-deficient hydroxylapatite which has a structure similar to that established during the setting and hardening of the biocement D. The preferred $CO_2$ content for the TCP of the present invention is about 0.2 to 10%. Such a material should be more suitable as a nucleating agent for the reaction of the biocement D. The preparation of the PHA is most simply carried out by conversion of three salts according to the following reaction:

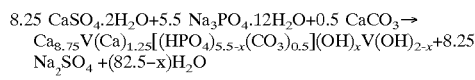

$$8.25\ CaSO_4 \cdot 2H_2O + 5.5\ Na_3PO_4 \cdot 12H_2O + 0.5\ CaCO_3 \rightarrow$$
$$Ca_{8.75}V(Ca)_{1.25}[(HPO_4)_{5.5-x}(CO_3)_{0.5}](OH)_xV(OH)_{2-x} + 8.25\ Na_2SO_4 + (82.5-x)H_2O$$

Instead of the $CaSO_4 \cdot 2H_2O$, other calcium salts of strong acids, such as, for example, an anhydrate or hydrate of calcium chloride or calcium nitrate, can also be used. However, the disadvantage thereof is the high deviation from stoichiometry, so that it is not possible to predict with certainty how much calcium is contained proportionately in the three salts.

In order to obtain a cation-deficient hydroxylapatite, the solution should have a pH between about 7 and 9, preferably between about 7 and 8. This is best achieved by dissolving $Na_2HPO_4$ or $K_2HPO_4$ or $NaH_2PO_4$ or $KH_2PO_4$ or a mixture thereof in an aqueous solution, in which the three above-mentioned salts are then correspondingly dissolved. The primary salts of phosphoric acid additionally have the advantage that they liberate $CO_2$ from the $CaCO_3$ of the biocement D powder mixture and thus enlarge or increase its porosity, which makes it possible to increase the remodelling rate.

A further precondition is the particle size of the PHA. In order for it to be suitable as a nucleating agent in biocement D, H or F (cf. DE 19813614.5), the particle size should be between about 0.5 and 10 μm, preferably between about 0.5 and 5 μm. This is achieved by dissolving magnesium chloride and/or magnesium sulfate and/or magnesium nitrate and/or one or more of their hydrates in an aqueous solution in which the reaction to give the PHA is carried out and in which the magnesium salts are dissolved, preferably before the three salts according to the above-mentioned equation are mixed in. The precipitate of PHA in the solution should be stored for a relatively long time at room temperature in order to complete the incorporation of the carbonate anions into the PHA. In order to avoid crystal growth of the precipitate increases in temperature should be avoided. Thereafter, the precipitate is removed from the aqueous solution, for example by filtration or centrifuging, the precipitate being washed with an excess of an aqueous solution comprising a neutral electrolyte, in order to remove sodium and sulfate ions. Traces of these ions in the PHA of the order of magnitude of about<0.1% by weight are acceptable. Preferably Na or K salts, in the form of chlorides and/or sulfates and/or nitrates and/or one or more of their hydrates, are used as neutral electrolytes. The reason for using these neutral electrolytes in the wash solution is to prevent the swelling and the disproportionation of the precipitate. After washing of the precipitate, it is dried overnight at about 120° C. In order to avoid aggregation, the drying should not be carried out for more than 16 h. The PHA thus prepared is then ready for use for the preparation of the final biocement D powder.

The PHA according to the invention can be used not only for the preparation of biocement D but also for the preparation of cement mixtures F and H. The compositions and mixing ratios of the biocements D, F and H are disclosed in WO 99/49906. As already mentioned above, however, a PHA of a different composition was used in these biocements.

In a preferred embodiment, the content of PHA is about 1 to 5% by weight, based on the total dry mass. More preferably, the PHA content is about 1.7 to 2.7% by weight, based on the total dry mass of the biocement.

Suitable compounds which can be mixed with TCP are in general all inorganic compounds which comprise calcium and phosphate. The compounds which are selected from the following group are preferred:
$CaHPO_4$, carbonate-containing apatite and $CaCO_3$.

The mixtures according to the invention can, if desired, also comprise known setting accelerators. Disodium hydrogen phosphate is preferred here.

Furthermore, it is desirable to mix with the mixture pharmaceutical active ingredients which have a very wide range of actions. Examples of such active ingredients are growth factors, such as FGF (Fibroblast Growth Factor), BMP (Bone Morphogenetic Protein), a growth factor from the TGF-β super family, TGF-β (Tissue Growth Factor), or other active ingredients, such as prostaglandins. Owing to their structure, the biocements are capable of releasing the active ingredients into the environment within a few days after the implantation.

Furthermore, it is useful to add antibiotics or disinfectants to the mixture according to the invention, as temporary protection from population with germs during the implantation, analogously to the known mixtures according to WO 99/49906.

The invention also relates to a corresponding mixture in the form of an aqueous solution, paste or suspension and its use for the preparation of biodegradable implantable synthetic bone materials.

In the foregoing and in the following examples, all temperatures are set forth uncorrected in degrees Celsius; and, unless otherwise indicated, all parts and percentages are by weight.

The entire disclosure of all applications, patents and publications, cited above and below, and of corresponding European Application No. 00110045.2, filed May 12, 2000 is hereby incorporated by reference.

The PHA is prepared according to the following example.

EXAMPLE

Three salts are combined in the following amounts and homogeneously mixed.

40.67 g of $CaSO_4.2H_2O$+60.0 g of $Na_3PO_4.12H_2O$+0.96 g of $CaCO_3$

This mixture is transferred to a 600 ml beaker. 200 ml of an aqueous solution consisting of 20 g of $Na_2HPO_4.2H_2O$+5 g of $MgCl_2.6H_2O$+20 g of $K_2HPO_4$ per 1 000 ml are then added. The solution is stirred at room temperature for 2 h. The precipitate is separated from the solution by means of filtration. The precipitate is then washed 20 times with, in each case, 50 ml of a 0.9% NaCl solution. Drying of the precipitate is then carried out overnight at 120° C. No aggregation is observed. The X-ray diffraction pattern indicated the structure of a microapatite. The FT-IR spectrum showed characteristic apatite and carbonate bonds of the B type.

Tab. 1 shows the compressive strength (in MPa) of the present invention after 2, 4, 6, 18, 72 and 240 hours in comparison with WO 99/49906 (biocement D).

TABLE 1

| Time [h] | Compressive strength WO 99/49906 (Biocement D) | Compressive strength Invention |
|---|---|---|
| 2 | 16 | |
| 4 | 26 | |
| 6 | | 29.2 |
| 18 | 45 | 46 |
| 72 | 47 | 74.3 |
| 240 | 48 | 75.5 |

FIG. 1 shows the values from table 1 graphically.

The results show that the object of the invention is achieved and the compressive strength of the PHA according to the invention after about 48 h has substantially higher values compared with the prior art.

The compressive strength was determined using a Lloyd material tester of the type LR50K after immersion for 2, 4, 6, 18, 72 and 240 hours in Ringer's solution. The reaction product is determined by means of X-ray diffractometry.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A mixture of powders suitable for preparation of absorbable calcium phosphate cements comprising:
    tricalcium phoshate (TCP) in which,
        30 to 70% of the TCP particles have a particle size of 0.1 to 7 um and
        10 to 60% of the TCP particles have a particle size of 40 to 100 um;
    precipitated hydroxylapatite (PHA) wherein the PHA is a cation-deficient hydroxylapatite of the formula I $$Ca_{8.75}V(Ca)_{1.25}[(HPO_4)_{5.5-x}(CO_3)_{0.5}](OH)_xV(OH)_{2-x}$$

in which x is 0–2; and
    at least one other phosphate-containing inorganic compound.

2. A mixture according to claim 1, wherein said mixture after hardening has a compressive strength of between 70–80 Mpa.

3. A mixture according to claim 1, wherein the PHA has a particle size of 0.5–10 um.

4. A mixture according to claim 3, wherein the PHA has a particle size of 0.5–5 um.

5. A mixture according to claim 1, wherein the PHA content is from 1–5% by weight, based on the total dry mass.

6. A mixture according to claim 1, wherein the PHA content is from 1.7–2.7% by weight, based on the total dry mass.

7. A mixture according to claim 1, wherein said at least one other phosphate-containing inorganic compound is selected from $CaHPO_4$ and carbonate-containing apatite.

8. A mixture according to claim 1, additionally comprising a setting accelerator.

9. A mixture according to claim 1, additionally comprising a pharmaceutically active ingredient.

10. A mixture according to claim 9, wherein said pharmaceutically active ingredient is an antibiotic or disinfectant.

11. A mixture according to claim 1, present in the form of an aqueous solution, suspension or paste.

12. A biodegradable implant produced from a hardened mixture according to claim 11.

13. A method of preparing biodegradable implantable synthetic bone materials comprising, hardening a mixture according to claim 1.

14. A mixture according to claim 9, wherein said pharmaceutically active ingredient is a growth factor or a prostaglandin.

15. A mixture according to claim 14, wherein said growth factor is a bone morphogenic protein, a tissue growth factor, a fibroblast growth factor, or a growth factor from the TGFβ superfamily.

16. An absorbable calcium phosphate cement paste comprising cement powders according to claim 1, and a liquid phase.

17. A kit for the preparation of a bio-cement paste comprising a mixture of powders according to claim 1, a pharmaceutical active ingredient and a liquid phase.

18. A mixture according to claim 1, wherein said precipitated hydroxylapatite (PHA) is prepared by:
   homogenously mixing CaSO4, $Na_3PO4$, and $CaCO_3$ in an aqueous solution;
   dissolving at least one magnesium salt into aqueous solution;
   removing resultant precipitate; and
   washing with a neutral electrolyte.

19. A mixture according to claim 18, wherein said at least one magnesium salt is magnesium chloride, magnesium sulfate, magnesium nitrate or one or more of their hydrates.

20. A method of repairing bone fractures comprising applying an absorbable calcium phosphate paste according to claim 16, to a bone fracture.

21. A method of preparing a mixture of powders according to claim 1, comprising:
   preparing said precipitated hydroxylapatite (PHA) by homogenously mixing CaSO4, $Na_3PO4$, and $CaCO_3$ in an aqueous solution,
   dissolving at least one magnesium salt into said aqueous solution,
   removing resultant precipitate, and
   washing said precipitate with a neutral electrolyte; and
   combining said precipitated hydroxylapatite with said tricalcium phoshate (TCP) and said at least one other phosphate-containing inorganic compound.

22. A method according to claim 21, wherein said at least one magnesium salt is magnesium chloride, magnesium sulfate, magnesium nitrate or one or more of their hydrates.

23. A mixture of powders suitable for preparation of absorbable calcium phosphate cements comprising:
   tricalcium phoshate (TCP) in which,
      30 to 70% of the TCP particles have a particle size of 0.1 to 7 um and
      10 to 60% of the TCP particles have a particle size of 40 to 100 um;
   precipitated hydroxylapatite (PHA) wherein the PHA is a cation-deficient hydroxylapatite of the formula I $Ca_{8.75}V(Ca)_{1.25}[(HPO_4)_{5.5-x}(CO_3)_{0.5}](OH)_xV(OH)_{2-x}$ in which x is 0–2; and
   $CaCO_3$.

* * * * *

UNITED STATES PATENT AND TRADEMARK OFFICE
CERTIFICATE OF CORRECTION

PATENT NO.   : 6,495,156 B2  
DATED        : December 17, 2002  
INVENTOR(S)  : Robert Wenz et al.

It is certified that error appears in the above-identified patent and that said Letters Patent is hereby corrected as shown below:

<u>Title page,</u>
Item [30], please insert -- May 12, 2000, (DE) No. 01110045.2 --

<u>Column 4,</u>
Line 34, reads "tricalcium phoshate" should read -- tricalcium phosphate --

<u>Column 5,</u>
Line 20, reads "pharmaceutical," should read -- pharmaceutically --
Line 23, reads "CaSO4, Na3PO4" should read -- $CaSO_4$, $NA_3PO_4$ --

<u>Column 6,</u>
Line 7, reads "CaSO4, Na3PO4" should read -- $CaSO_4$, $NA_3PO_4$ --
Lines 14 and 21, reads "tricalcium phoshate" should read -- tricalcium phosphate --

Signed and Sealed this

Twenty-fifth Day of May, 2004

JON W. DUDAS  
*Acting Director of the United States Patent and Trademark Office*